United States Patent [19]

Obikawa

[11] Patent Number: 5,026,879

[45] Date of Patent: Jun. 25, 1991

[54] 1,3-DIOXANE DERIVATIVES AND COMPOSITION INCLUDING SAME

[75] Inventor: Tsuyoshi Obikawa, Suwa, Japan

[73] Assignee: Seiko Epson Corporation, Tokyo, Japan

[21] Appl. No.: 500,985

[22] Filed: Mar. 20, 1990

[30] Foreign Application Priority Data

Apr. 28, 1989 [JP] Japan .................... 1-109649

[51] Int. Cl.⁵ ................. C07D 319/06; G02F 1/13; C09K 3/24
[52] U.S. Cl. ................ 549/369; 252/299.61
[58] Field of Search ................ 549/369; 252/299.61

[56] References Cited

U.S. PATENT DOCUMENTS

| | | | |
|---|---|---|---|
| 4,323,473 | 4/1982 | Sethofer | 252/299.61 |
| 4,323,504 | 4/1982 | Sethofer | 549/369 |
| 4,348,324 | 9/1982 | Demus et al. | 549/369 |
| 4,871,469 | 10/1989 | Reiffenrath et al. | 252/299.61 |

*Primary Examiner*—Nicky Chan
*Attorney, Agent, or Firm*—Blum Kaplan

[57] ABSTRACT 2-(3', 4'-difluorophenyl)-1,3-dioxane derivatives represented by the general formula:

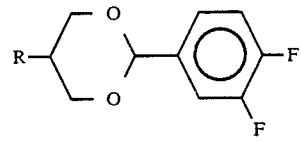

wherein R is a linear alkyl group having from 1 to 8 atoms, and having large positive dielectric constant anisotropy ($\Delta\epsilon$) and small refractive index anisotropy ($\Delta n$). The dioxane derivatives may be included in liquid crystal compositions for improved display devices having a low threshold voltage, a low driving voltage and a wide visual angle.

13 Claims, No Drawings

1,3-DIOXANE DERIVATIVES AND COMPOSITION INCLUDING SAME

BACKGROUND OF THE INVENTION

This invention relates to 2-(3',4'-difluorophenyl)-1,3-dioxane derivatives, and more particularly to novel liquid crystal compositions including 2-(3',4'-difluorophenyl)-1,3-dioxane derivatives suitable for use in electro-optical displays.

Liquid crystal display devices utilize electro-optical effects possessed by liquid crystals. The liquid crystal materials used in these devices have a nematic phase, a cholesteric phase and a smectic phase. The most widely used display mode uses liquid crystal materials in the nematic phase and includes the dynamic scattering type (DSM), guest-host type (G-H), twisted nematic type (TN), super-twisted nematic type (STN), super-twisted birefringence type (SBE) modes and the like. The driving systems used for these liquid crystal display devices include the static driving system, time-sharing driving system (simple matrix driving system), active matrix driving system, two frequency driving system and the like.

Liquid crystal display devices have several advantages, particularly liquid crystal display devices using liquid crystal materials in the twisted nematic or super twisted nematic modes or the like. The devices are small in size and can be made thin and the devices can be driven at low voltage with low power consumption. The liquid crystal material is a light receiving element so that when a liquid crystal display is viewed over a long time, eye strain does not occur.

In view of these benefits, liquid crystal display technology has been applied to watches, cameras, electronic counters, audio equipment, automobile dashboard indicators, telephone equipment, measuring devices and the like. More particularly, liquid crystal display devices have also been utilized recently in personal computers and word processor displays and in other devices including displays which require high resolution and many pixels, including televisions and the like. Thus, liquid crystal display devices continue to attract attention as potentially replacing cathode ray tubes. As a result, liquid crystal display devices are in a wide variety of areas, and it is likely that their use will be broadened further.

For practical use, liquid crystal compositions must possess the following characteristics:
1. The liquid crystal materials must be colorless and thermally, optically, electrically and chemically stable;
2. Have a wide nematic temperature range;
3. Have a low threshold voltage ($V_{th}$);
4. The temperature dependency of threshold voltage be small;
5. A wide visual angle; and
6. Have a rapid electro-optical response speed.

Many liquid crystal materials possess one of the above-desired properties, however, no single compound satisfies at least two of the above-desired properties. Thus, liquid crystal compositions are formed of several different liquid crystal compounds or liquid crystal compositions are obtained by mixing liquid crystal compounds with pseudo liquid crystal compounds to obtain the desired properties. The pseudo liquid crystal compounds are compounds resembling liquid crystal compounds in their molecular formulas, but fail to manifest liquid crystal phases.

In particular, since the integrated circuit (IC) driving the liquid crystal display device has limited resistance to voltage, when a liquid crystal display device is operated with a power source or is a large scale time-sharing device, it is desirable to decrease the driving voltage of the liquid crystal display device. In order to decrease the driving voltage of a liquid crystal display device, it is necessary to decrease the threshold voltage ($V_{th}$) as much as possible, since $V_{th}$ represents the driving voltage. Generally, $V_{th}$ is reduced by including a compound having a large positive dielectric constant anisotropy ($\Delta\epsilon$). These compound include, for example:

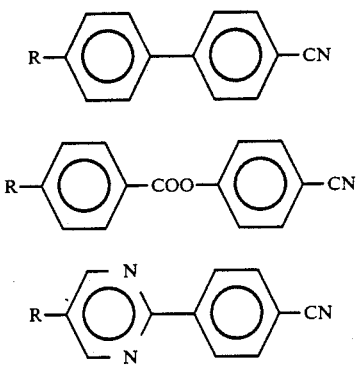

wherein R is a linear alkyl or alkoxy group.

These conventional compounds, however, also have large refractive index anisotropy ($\Delta n$). The visual angle is dependent upon the pre-tilt of the liquid crystal molecule and the visual angle range widens as $\Delta n$ decreases and narrows as $\Delta n$ increases. Thus, these conventional compounds have a narrow visual angle and narrow the visual angle of a liquid crystal display device in which they are included and are not completely satisfactory.

Accordingly, it is desirable to provide an improved liquid crystal material for use in a nematic liquid crystal composition having a low threshold voltage and a small refractive index anisotropy.

SUMMARY OF THE INVENTION

Generally speaking, in accordance with the invention, 2-(3',4'-difluorophenyl)-1,3-dioxane derivatives represented by the general formula:

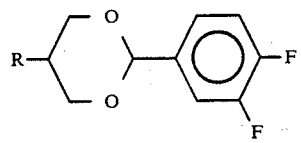

wherein R is a linear alkyl group having from 1 to 8 carbon atoms are provided. The 1,3-dioxane ring is either the cis or trans isomer. Preferably, in a mixture of the cis and trans isomers, at least 60% of the 1,3-dioxane rings are the trans isomer.

The 2-(3',4'-difluorophenyl)-1,3-dioxane derivatives have large positive dielectric constant anisotropy and small refractive index anisotropy. The 2-(3',4'-difluorophenyl)-1,3-dioxane derivatives may be mixed with other liquid crystal compounds to obtain liquid crystal display devices having a low driving voltage and a wide visual angle.

Accordingly, it is an object of the invention to provide an improved liquid crystal compound.

It is another object of the invention to provide 2(3′,4′-difluorophenyl)-1,3-dioxane derivatives.

It is a further object of the invention to provide 2(3′,4′-difluorophenyl)-1,3-dioxane derivatives suitable for use as ingredients in liquid crystal compositions utilized as electro-optical display materials.

Still another object of the invention is to provide liquid crystal compositions including 2-(3′,4′-difluorophenyl)-1,3dioxane derivatives suitable for use in TN cells.

Still a further object of the invention is to provide improved liquid crystal compositions including 2-(3′,4′-difluorophenyl)-1,3-dioxane derivatives for lowering the driving voltage and widening the visual angle.

Yet a further object of the invention is to provide a method for preparing improved 2-(3′,4′-difluorophenyl)-1,3-dioxane derivatives.

Yet another object of the invention is to provide improved liquid crystal display devices including liquid crystal compositions including 2-(3′,4′-difluorophenyl)-1,3-dioxane derivatives.

Still other objects and advantages of the invention will in part be obvious and will in part be apparent from the specification.

The invention accordingly comprises of several steps and the relation of one or more of such steps with respect to each of the others thereof, which will be exemplified in the compounds, compositions, method and device hereinafter disclosed, and the scope of the invention will be indicated in the claims.

DESCRIPTION OF THE PREFERRED EMBODIMENTS

The liquid crystal compounds prepared in accordance with the invention are 2-(3′,4′-difluorophenyl)-1,3-dioxane derivatives represented by the general formula as follows:

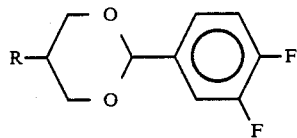

wherein R is a linear alkyl group having from 1 to 8 carbon atoms. The 1,3-dioxane ring is either the cis or the trans isomer. Preferably, in a mixture of cis and trans isomers, at least 60% of the 1,3-dioxane rings are trans isomers.

The 2-(3′,4′-difluorophenyl)-1,3-dioxane derivatives have large positive dielectric constant anisotropy and small refractive index anisotropy.

The 2-(3′,4′-difluorophenyl)-1,3-dioxane derivatives can be produced by the following Reaction Scheme I:

REACTION SCHEME I

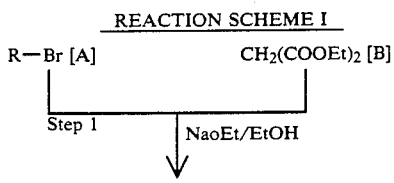

-continued
REACTION SCHEME I

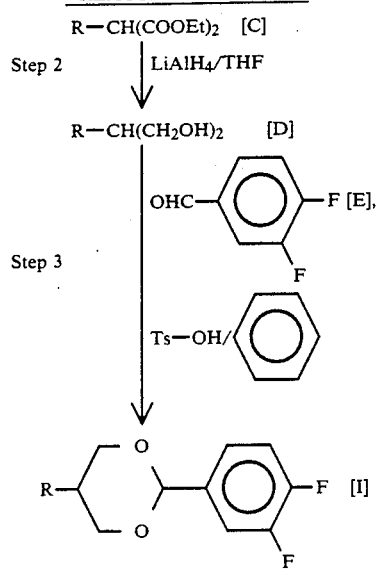

In ethanol, compound [A], a bromoalkane, is reacted with compound [B], a diethyl malonate, in the presence of sodium ethoxide to yield compound [C], a diethyl alkylmalonate. In tetrahydrofuran, compound [C] is reduced with lithium aluminum hydride to yield compound [D], a 2-alkylpropane-1,3-diol.

Compound [D] and compound [E], 3,4-difluorobenzaldehyde are dissolved in a solvent of methylene chloride, chloroform, benzene, or toluene, or the like, which are capable of forming an azeotropic mixture with water. The resulting solution is refluxed in the presence of p-toluenesulfonic acid, sulfuric acid, or an H-forming cation-exchange resin acting as a catalyst. While the solution is refluxed, water formed is removed using a water separator to yield a novel liquid crystal compound in accordance with the invention.

The 1,3-dioxane derivatives produced using the reaction scheme illustrated above are a mixture of 1,3-dioxane derivatives wherein the 1,3-dioxane ring is the trans isomer and 1,3-dioxane derivatives wherein the 1,3-dioxane ring is the cis isomer. The ratio of formation of these isomers varies depending upon reaction temperature, reaction time, type of solvent and the like. The proportion of the trans isomer is generally greater than the cis isomer. Preferably, the 1,3-dioxane derivative is the trans isomer. However, separation of the trans isomer from the cis isomer is difficult. Thus, for practical purposes, the mixture of the trans isomer and the cis isomer obtained from the above reaction scheme is used without further modification. Preferably, the mixture includes at least 60% of the trans isomer.

The following examples are set forth by way of illustration to show preparation of the 1,3-dioxane derivatives in accordance with the invention. They are set forth for purposes of illustration only, and are not intended in a limiting sense.

EXAMPLE 1

Production of
5-pentyl-2-(3′,4′-difluorophenyl)-1,3dioxane (mixture of the trans isomer and the cis isomer)

Step 1

23 g (1.0 mol) of metallic sodium was dissolved in 500 cm³ of anhydrous ethanol and 160 g (1.0 mol) of diethyl malonate and 151 g (1.0 mol) of 1-bromopenate were added and the solution was stirred. The solution was refluxed for 7 hours. The product of the reaction was cooled to room temperature and filtered to separate the sodium bromide produced. The ethanol in the filtrate was distilled out. The residue was dissolved in 500 cm³ of chloroform and the resulting solution was sequentially washed with water, 5% hydrochloric acid, and water. The chloroform was distilled off. The residual oily substance was subjected to vacuum distillation (b.p. 103° C./3 Torrs) to yield 193 g (0.84 mol) of diethyl pentylmalonate.

Step 2

35 g (0.92 mol) of lithium aluminum hydride was dispersed in 420 cm² of anhydrous tetrahydrofuran (THF) and 193 g (0.84 mol) of diethyl pentylmalonate was added drop-wise to the dispersion while stirring at a speed to gently reflux the THF. The solution was refluxed and stirred for 3 hours. The product of the reaction was cooled with water and THF containing 10% water was added until the mixture ceased to foam. 500 cm² of concentrated hydrochloric acid was added. The oily layer was separated and the water layer was extracted three times with 200 cm³ of ether. The oily layer and the ether layers were combined and washed with a saturated aqueous solution of sodium chloride. The ether layer was dried with anhydrous sodium sulfate and boiled to distil off the ether. The residue of the distillation was subjected to vacuum distillation (b.p. 120° C./2 Torrs) to yield 83 g (0.57 mol) of 2-pentylpropane-1,3-diol.

Step 3

83 g (0.57 mol) of the 2-pentylpropane-1,3-diol, 81 g (0.57 mol) of 3,4-difluorobenzaldehyde (manufactured by Aldrich Corp.), and 4.9 (0.02 mol) of p-toluenesulfonic acid was dissolved in 285 cm³ of benzene. The solution was refluxed for 5 hours, and the water formed was removed with a water separator. The solution was sequentially washed with water, an aqueous 5% NaHCO₃ solution, and water and the solution was boiled to distill off the benzene. The residual oily substance formed was subjected to vacuum distillation (b.p. 140° C./3.5 Torrs) to yield 121 g (0.45 mol) of a mixture of the trans and a cis isomers of 5-pentyl-2-(3',4'-difluorophenyl)-1,3-dioxane. The mixture was 80% of the trans isomer and 20% of the cis isomer. The mixture was an isotropic liquid at room temperature.

The following are other examples of the compounds in accordance with this embodiment of the invention which may be prepared following the procedures of Example 1.

5-methyl-2-(3',4'-difluorophenyl)-1,3-dioxane
5-ethyl-2-(3',4'-difluorophenyl)-1,3-dioxane (trans:-cis=70:30), b.p. 110° C./3 mmHg
5-propyl-2-(3',4'-difluorophenyl)-1,3-dioxane (trans:-cis=75:25), b.p. 120° C./3 mmHg
5-butyl-2-(3',4'-difluorophenyl)-1,3-dioxane (trans:-cis=77:23), b.p. 128° C./3 mmHg
5-hexyl-2-(3',4'-difluorophenyl)-1,3-dioxane (trans:-cis=81:19), b.p. 150° C./4 mmHg
5-heptyl-2-(3',40 -difluorophenyl)-1,3-dioxane (trans:-cis=81:19), b.p. 164° C./4 mmHg
5-octyl-2-(3',4'-difluorophenyl)-1,3-dioxane (trans:-cis=80:20), b.p. 173° C./3 mmHg Each of the above mixtures was an isotropic liquid at room temperature.

EXAMPLE 2

Effect of the solvent used in the preparation of 5-pentyl-2-(3',4'-difluorophenyl)-1,3,-dioxane:

Four solutions were prepared by dissolving 11.8 g (0.10 mol) of 2-pentylpropane-1,3-diol (prepared in Example 1 following the procedures of Steps 1-2), 14.2 g (0.10 mol) of 3,4-difluorobenzaldehyde, and 0.9 g (0.005 mol) of p-toluenesulfonic acid in methylene chloride (b.p. 40° C.), chloroform (b.p. 60° C.), benzene (b.p. 80° C.) and toluene (b.p. 111° C.), respectively. The solutions were treated following the procedures of Step 3 of Example 1 to yield mixtures of the cis and trans isomers of 5-pentyl-2-(3',4'-difluorophenyl)-1,3-dioxane. The yields of each mixture from its respective solvent and the ratio of the trans isomer to the cis isomer of each mixture are shown in Table 1.

TABLE 1

| Solvent | b.p. (°C.) | Trans:cis | Yield (%) |
|---|---|---|---|
| Methylene chloride | 40.1 | 86:14 | 85 |
| Chloroform | 61.2 | 84:16 | 87 |
| Benzene | 80.1 | 80:20 | 84 |
| Toluene | 110.6 | 68:32 | 86 |

Table 1 shows that each of the mixtures of the cis and trans isomers of 5-pentyl-2-(3',4'-difluorophenyl)-1,3-dioxane includes at least 60% of the trans isomer. Generally, the proportion of the cis isomer formed increases as the length of the alkyl group (R) decreases.

EXAMPLE 3

Separation of the trans isomers from mixtures of cis and trans 5-alkyl-2-(3',4'-difluorophenyl)-1,3-dioxane derivatives prepared in Example 1.

First, separation of the cis and trans isomers was attempted using recrystallization. However, this was in vain. Next, separation was attempted with a fractionation liquid chromatograph (Hitachi Model 655) and a reverse phase column, C18 type, measuring 5 cm in diameter and 25 cm in length (produced by Merck) and using a particulate filter with a 7 μm diameter. The solvent was a solvent mixture of 85% methanol and 15% water. However, even with this method, separation could not be effected for compounds wherein R was—C₂H₅. The melting points (m.p.) of the trans-5-alkyl-2-(3',4'-difluorophenyl)-1,3-dioxane derivatives prepared following the procedures of Example 3 are shown in Table 2.

TABLE 2

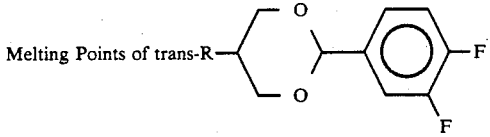

Melting Points of trans-R

| R | m.p. (°C.) |
|---|---|
| $C_3H_7$ | 5 |
| $C_4H_9$ | 0 |
| $C_5H_{11}$ | 3 |
| $C_6H_{13}$ | −4 |
| $C_7H_{15}$ | −7 |
| $C_8H_{17}$ | −5 |

EXAMPLE 4

Trans-5-pentyl-2-(3',4'-diflourophenyl)-1,3-dioxane and cis-5-pentyl2-(3',4'-diflourophenyl)-1,3-dioxane (prepared in Example 3) were mixed in six different ratios of 100:0 (trans:cis), 80:20, 60:40, 40:60, 20:80, and 0:100. Liquid crystal compositions, A-0, A-20, A-40, A-60, A-80, and A-100, were prepared by mixing 10% by weight of each of the above mixtures, respectively, in ZLI-1565, a commercially available liquid crystal composition (produced by Merck). The nematic phase-isotropic liquid transition point (N-I point) was measured for each of the liquid crystal compositions and the results are shown in Table 3.

TABLE 3

| Composition | trans:cis | N-I point (°C.) |
|---|---|---|
| A-0 | 100:0 | 71 |
| A-20 | 80:20 | 65 |
| A-40 | 60:40 | 52 |
| A-60 | 40:60 | 28 |
| A-80 | 20:80 | 10 |
| A-100 | 0:100 | Isotropic liquid |

In Example 3, separation of the trans component was performed with a fractionation liquid chromatograph. Practically, however, separation of trans-5-alkyl-2-(3',4'-difluorophenyl)-1,3-dioxane from cis-5-alkyl-2-(3',4'-difluorophenyl)-1,3-dioxane with a fractionation liquid chromatograph is not feasible in terms of cost and production efficiency. Thus, the production of a practicable liquid crystal composition requires the mixture of the cis isomer and the trans isomer to be utilized in the ratio produced. However, as shown in Table 3, the N-I point is very low when the percentage of the cis isomer is very large. In practice, the N-I point must be at least 50° C. Thus, it is preferable that mixtures of cis and trans isomers of the 1,3-dioxane derivatives include not more than 40% of the cis isomer, and not less than 60% of the trans isomer.

EXAMPLE 5

Liquid crystal compositions [B] and [C] were prepared by mixing 10% by weight of trans-5-pentyl-2-(3',4'-difluorophenyl)1,3-dioxane in 90% by weight of ZLI-1565 and 10% by weight of an 80:20 (trans:cis) mixture of trans and cis 5-pentyl-2-(3',4'-difluorophenyl)-1,3-difluorophenyl)-1,3-dioxane in 90% weight of ZLI-1565.

Liquid crystal composition [B]

ZLI-1565     90 wt %

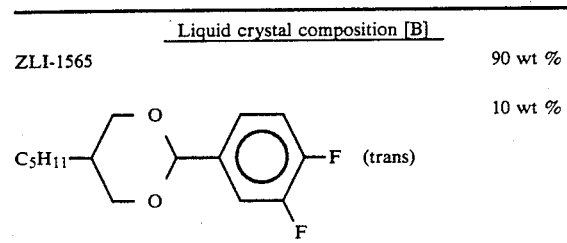

10 wt % (trans)

Liquid crystal composition [C]

ZLI-1565     90 wt %

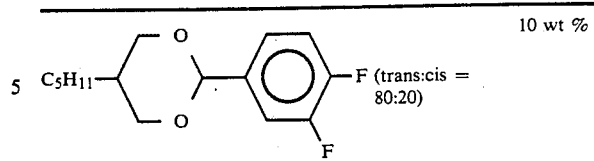

10 wt % F (trans:cis = 80:20)

For comparison, liquid crystal compositions [D] and [E] were prepared by mixing 10 weight percent of

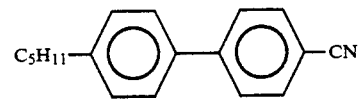

and

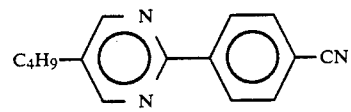

in 90 weight percent of ZLI-1565, respectively.

Liquid crystal composition [D]

ZLI-1565     90 wt %

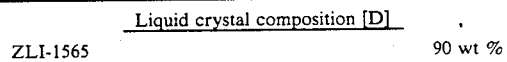

10 wt %

Liquid crystal composition [E]

ZLI-1565     90 wt %

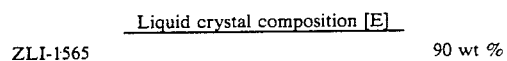

10 wt %

The refractive index anisotrophy ($\Delta n$) of each of the composition was measured. Each composition was sealed in a 8 μm thick twisted nematic liquid crystal cell. The voltage-luminance characteristic was measured under static driving conditions to determine the threshold voltage, $V_{th}$ (voltage required for 10% luminance). The results are shown in Table 4.

TABLE 4

| Composition | $\Delta n$ | $V_{th}$ (V) |
|---|---|---|
| [B] | 0.128 | 1.80 |
| [C] | 0.127 | 1.85 |
| [D] | 0.143 | 1.80 |
| [E] | 0.138 | 1.75 |

While the invention has been described in detail with reference to ZLI-1565, it is understood that the decrease in the threshold voltage and decrease in the refractive index anisotropy can be obtained with other compatible liquid crystal compositions, including:

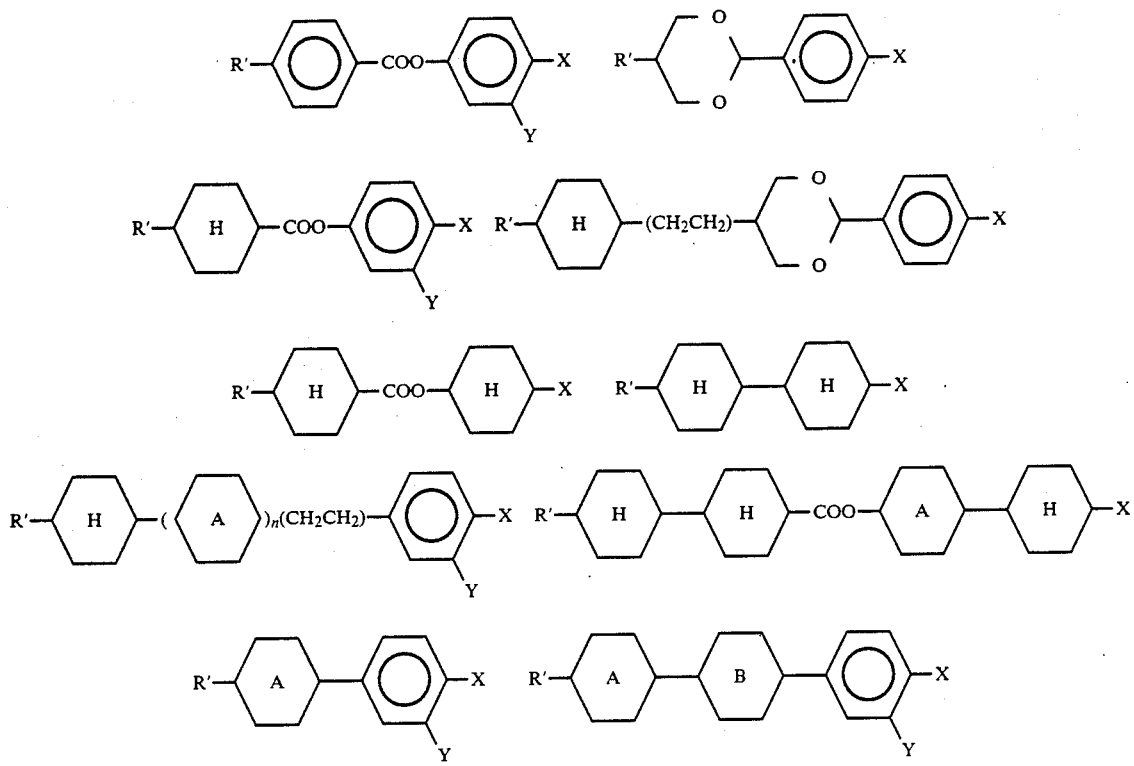

wherein R' is a straight chain alkyl group or alkoxy group, X is a straight chain alkyl group, alkoxy group, F or CN, Y is H, F or Cl,

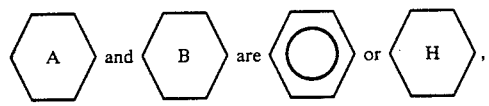

n is 0, 1 or 2, and m is 0 or 1.

The 2-(3',4'-difluorophenyl)-1,3-dioxane derivatives are included in the liquid crystal composition in at least a minimum effective amount to decrease the driving voltage and widen the visual angle as desired up to about 50 weight percent based on the total weight of the composition. Preferably, between about 3 and 20 weight percent is added and most preferably 7 to 15 weight %.

As described above, the 2-(3',4'-difluorophenyl)-1,3-dioxane derivatives in accordance with the invention have a large positive dielectric anisotropy and small refractive index anisotropy. Liquid crystal compositions having a low driving voltage and wide visual angle are obtained when liquid crystal compounds in accordance with the invention are mixed with conventional liquid crystal compositions. In particular, liquid crystal compositions having a wide temperature range are obtained when the 1,3-dioxane ring is at least 60% trans. Thus, the 1,3-dioxane derivatives are extremely useful as constituent components for liquid crystal compositions.

It will thus be seen that the objects set forth above, among those made apparent from the preceding description, are efficiently attained and, since certain changes may be made in carrying out the above embodiments and in the compositions set forth without departing from the spirit and scope of the invention, it is intended that all matter contained in the above description shall be interpreted as illustrative and not in a limiting sense.

It is also to be understood that the following claims are intended to cover all of the generic and specific features of the invention herein described and all statements of the scope of the invention, of which, as a matter of language, might be said to fall therebetween.

Particularly, it is to be understood that in said claims, ingredients or compounds recited in the singular are intended to include compatible mixtures of such ingredients wherever the sense permits.

What is claimed is:

1. A 2-(3',4'-difluorophenyl)-1,3-dioxane derivative having the general formula:

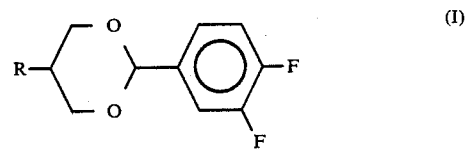

(I)

wherein R is a linear alkyl group having from 1 to 8 carbon atoms.

2. The 2-(3',4'-difluorophenyl)-1,3-dioxane derivative of claim 1, wherein the 1,3-dioxane ring is at least 60% of the trans isomer.

3. The 2-(3',4'-difluorophenyl)-1,3-dioxane derivative of claim 1, wherein the 1,3-dioxane ring is the trans isomer.

4. 5-pentyl-2-(3',4'-difluorophenyl)-1,3-dioxane represented by the formula:

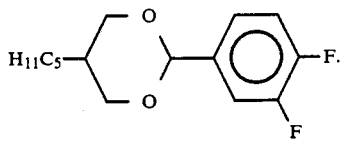

5. Trans-5-pentyl-2-(3',4'-difluorophenyl)-1,3-dioxane represented by the formula:

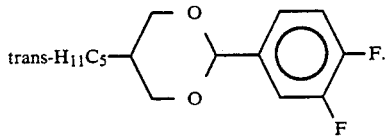

6. The 2-(3',4'-difluorophenyl)-1,3-dioxane derivative of claim 1, wherein the number of carbon atoms in R is between about 3 and 5.

7. A liquid crystal composition comprising an effective amount of at least one 2-(3',4'-difluorophenyl)-1,3-dioxane derivative for decreasing the threshold voltage and widening the visual angle, the 2-(3,4'-difluorophenyl)-1,3-dioxane derivative having the general formula:

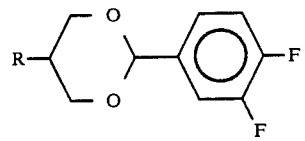

wherein R is a straight chain alkyl group having from 1 to 8 carbon atoms.

8. The liquid crystal composition of claim 7, wherein th dioxane derivative is present between about 1 and 50 weight percent.

9. The liquid crystal composition of claim 8, wherein the dioxane derivative is present between about 3 and 20 weight percent.

10. The liquid crystal composition of claim 7, wherein the dioxane derivative is 5-pentyl-2-(3',4'-difluorophenyl)-1,3dioxane.

11. The liquid crystal composition of claim 10, wherein the derivative is trans-5-pentyl-2-(3',4'-difluorophenyl)-1,3-dioxane.

12. The liquid crystal composition of claim 7, wherein the number of carbon atoms in R is between about 3 and 5.

13. A 5-alkyl-2-(3',4'-diflourophenyl)-3,3-dioxane derivative having the general formula:

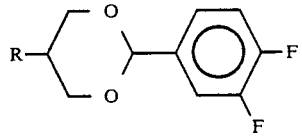

wherein R is a linear alkyl group having from 3 to 5 carbon atoms and the 1,3-dioxane ring is at least 60% of the trans isomer.

* * * * *